United States Patent
Misselbrook et al.

(10) Patent No.: US 10,136,637 B2
(45) Date of Patent: Nov. 27, 2018

(54) PESTICIDE NANO-SUSPENSION

(71) Applicant: AGFORM LIMITED, Hampshire (GB)

(72) Inventors: John Misselbrook, Hampshire (GB); Jeff Dunn, Hampshire (GB)

(73) Assignee: AGFORM LIMITED, Southhampton, Hampshire (GB)

( * ) Notice: Subject to any disclaimer, the term of this patent is extended or adjusted under 35 U.S.C. 154(b) by 0 days.

(21) Appl. No.: 14/431,800

(22) PCT Filed: Sep. 24, 2013

(86) PCT No.: PCT/GB2013/052497
§ 371 (c)(1),
(2) Date: Mar. 27, 2015

(87) PCT Pub. No.: WO2014/049347
PCT Pub. Date: Apr. 3, 2014

(65) Prior Publication Data
US 2015/0272113 A1    Oct. 1, 2015

(30) Foreign Application Priority Data

Sep. 28, 2012  (GB) .................................. 1217441.3

(51) Int. Cl.
*A01N 25/04* (2006.01)
*A01N 43/40* (2006.01)
*A01N 47/30* (2006.01)
*A01N 25/30* (2006.01)

(52) U.S. Cl.
CPC ............. *A01N 25/04* (2013.01); *A01N 25/30* (2013.01); *A01N 43/40* (2013.01); *A01N 47/30* (2013.01)

(58) Field of Classification Search
None
See application file for complete search history.

(56) References Cited

U.S. PATENT DOCUMENTS

| | | | | |
|---|---|---|---|---|
| 4,990,177 A * | 2/1991 | Hewett | .................. | A01N 47/30 504/130 |
| 5,013,353 A | 5/1991 | Hewett et al. | | |
| 2006/0135391 A1* | 6/2006 | Scheibel | .................. | A61K 8/87 510/421 |
| 2007/0081947 A1 | 4/2007 | Eble et al. | | |
| 2007/0107638 A1* | 5/2007 | Chun | .................. | C04B 24/06 106/729 |
| 2007/0122436 A1 | 5/2007 | Koltzenburg et al. | | |
| 2007/0142611 A1 | 6/2007 | Ohashi et al. | | |
| 2007/0244216 A1* | 10/2007 | Stern | .................. | A01N 25/10 523/122 |
| 2008/0047462 A1* | 2/2008 | Klein | .................. | B01F 17/0042 106/31.78 |
| 2010/0000883 A1* | 1/2010 | Morrin | .................. | C12Q 1/001 205/786 |
| 2010/0016392 A1* | 1/2010 | Kabanov | .................. | A01N 25/10 514/384 |
| 2010/0048655 A1* | 2/2010 | Koltzenburg | .......... | A01N 25/10 514/383 |
| 2011/0014255 A1 | 1/2011 | Balastre | | |
| 2011/0219983 A1* | 9/2011 | Baseeth | .............. | B01F 17/0085 106/31.75 |

FOREIGN PATENT DOCUMENTS

| | | |
|---|---|---|
| CN | 101486858 A | 7/2009 |
| JP | 2005-307185 A | 11/2005 |
| WO | 2003/039254 A1 | 5/2003 |
| WO | 2003/089523 A1 | 10/2003 |
| WO | 2005/087002 A2 | 9/2005 |
| WO | 2005/111160 A1 | 11/2005 |
| WO | 2005/113677 A1 | 12/2005 |
| WO | 2008/018873 A1 | 2/2008 |
| WO | 2008/032328 A2 | 3/2008 |
| WO | 2008/076807 A2 | 6/2008 |
| WO | 2011/037968 A1 | 3/2011 |
| WO | 2012/045994 A1 | 4/2012 |
| WO | 2014/049347 A1 | 4/2014 |

OTHER PUBLICATIONS

Huntsman. MSDS for Jeffsperse X3204. pp. 1-3. publication date: Jan. 19, 2006.*
Cerdeira et al. (Aug. 30, 2010) "Miconazole nanosuspensions: Influence of formulation variables on particle size reduction and physical stability," International Journal of Pharmaceutics. 396(1-2):210-218.
Chin et al. (Jun. 15, 2011) "New Approach to Pesticide Delivery Using Nanosuspensions: Research and Applications," Industrial & Engineering Chemistry Research. 50(12):7637-7643.
Elek et al. (Dec. 3, 2012) "Novaluron nanoparticles: Formation and potential use in controlling agricultural insect pests," Colloids and Surfaces A: Physicochemical and Engineering Aspects. 372(1-3):66-72.
Huntsman (2009) "Jeffsperse® X3503 Dispersant. A VOC-Free Dispersant for the Dispersion of Carbon Black and Organic Pigments in Water-Based Inks and Coatings," Huntsman Corporation Technical Bulletin. Accessed on the Internet at URL: http://www.huntsman.com/performance_products/Media%20Library/global/files/technical_bulletin_jeffsperse_x3503_0410.pdf. [Last Accessed Jul. 1, 2015].

(Continued)

*Primary Examiner* — Katherine Peebles
(74) *Attorney, Agent, or Firm* — Brian C. Trinque; Lathrop Gage LLP

(57) ABSTRACT

Many active agents, such as insecticides, herbicides and fungicides are relatively insoluble in aqueous media. In order to apply them efficiently to crops it is thus necessary to formulate them in a manner that facilitates their dilution in the water based spray media used in practice, by the farmer or contract spray operator. The present invention relates to aqueous dispersions of active agents such as insecticides, herbicides and fungicides, in particular such dispersions in which the particles are of sub-micron diameter.

16 Claims, 10 Drawing Sheets

(56) References Cited

OTHER PUBLICATIONS

Figure 1:
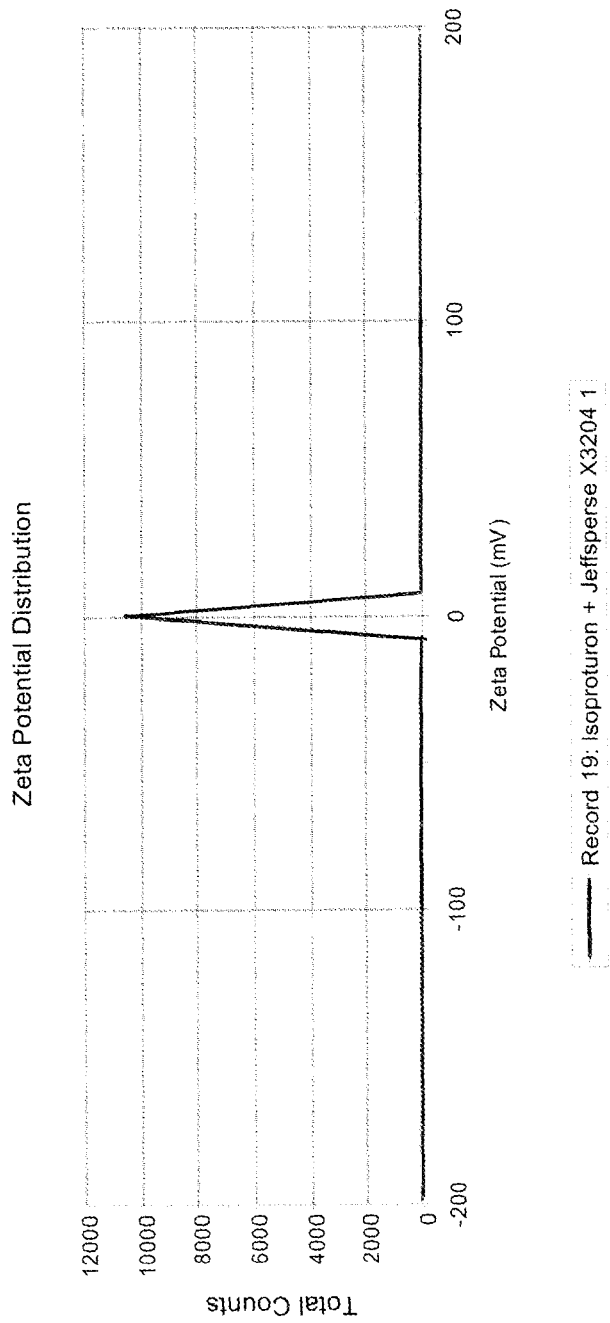

Kumar et al. (Jan. 1, 2011) "Nanosuspensions: The Solution to Deliver Hydrophobic Drugs," International Journal of Drug Delivery. 3:546-557.
Verma et al. (2009) "A comparative study of top-down and bottom-up approaches for the preparation of micro/nanosuspensions," International Journal of Pharmaceuticals. 380(1-2):216-222.
Zeng et al. (2009) "System Investigation of the Formation of Beta-Cypermethrin Nanosuspension: Influence of the Formulation Variables," Journal of Dispersion Science and Technology. 30(1):76-82.
International Preliminary Report on Patentability corresponding to International Patent Application No. PCT/GB2013/052497, completed Oct. 7, 2014, 18 pages.
International Search Report with Written Opinion corresponding to International Patent Application No. PCT/GB2013/052497, dated Feb. 28, 2014, 26 pages.

* cited by examiner

| EPPO Code | Scientific Name | Common Name |
|---|---|---|
| BRSNN | *Brassica napus* | Oilseed rape |
| CAPBP | *Capsella bursa-pastoris* | Sheperd's purse |
| CHEAL | *Chenopodium album* | Lambs quarters |
| CIRAR | *Cirsium arvense* | Creeping thistle |
| FUMOF | *Fumaria officinalis* | Common fumitory |
| GALAP | *Galium aparine* | Cleavers |
| MATSS | *Matricaria spp.* | Mayweed species |
| PAPSS | *Papaver spp.* | Poppy |
| PLASS | *Plantago spp.* | Plantain |
| POAAN | *Poa annua* | Annual meadowgrass |
| RUMOB | *Rumex obtusifolius* | Broad-leaf dock |
| SENVU | *Senecio vulgaris* | Common groundsel |
| SINAR | *Sinapis arvensis* | Wild mustard |
| STEME | *Stellaria media* | Common chickweed |
| URTDI | *Urtica spp.* | Nettle |
| VERSS | *Veronia spp.* | Speedwell species |

Figure 2

| Days After Application | Rate (l/ha) | 10-20 DA-A | 21-50 DA-A | 51-80 DA-A | >81 DA-A |
|---|---|---|---|---|---|
| | | Efficacy as mean % control (number of trials assessed at this timing) (minimum-maximum % control range) | | | |
| Blutron | | | | | |
| POAAN-Pre emergence | | | | | |
| Blutron (IPU 188g + DFF 37.5g) | 1.0 | 68.7 (3) (21.3-99.8) | 80.3 (9) (38.8-99) | 87.3 (3) (68-99.5) | 87 (10) (56.3-99.3) |
| Blutron (IPU 250g + DFF 50g) | 0.75 | 66.7 (3) (25-100) | 83 (9) (59.8-99.5) | 87 (3) (68.5-100) | 90.4 (10) (62.5-100) |
| POAAN-Post emergence | | | | | |
| Blutron (IPU 188g + DFF 37.5g) | 1.0 | 44 (7) (1 5-88.8) | 49.9 (8) (2.5-94.3) | 62.7 (8) (6.3-97.8) | 81.3 (6) (66.8-98.5) |
| Blutron (IPU 250g + DFF 50g) | 0.75 | 51.3 (7) (32.5-85.5) | 62.1 (8) (8.3-98.5) | 70.8 (8) (11.3-96.8) | 7 51 (6) (40-99.3) |
| Blutron plus | | | | | |
| POAAN-Pre emergence | | | | | |
| Blutron Plus (IPU 188g + DFF 75g) | 1.0 | 69 (3) (2 5-94.5) | 90 (9) (80-99.3) | 95 (3) (91.3-100) | 95.7 (10) (82.5-99.5) |
| Blutron Plus (IPU 250g + DFF 100g) | 0.75 | 71.7 (3) (30-100) | 94 (9) (82.5-99.8) | 97.7 (3) (95.3-99.5) | 96.2 (10) (77.5-100) |
| POAAN -Post emergence | | | | | |
| Blutron Plus (IPU 188g + DFF 75g) | 1.0 | 51.8 (7) (23.8-82.5) | 56.9 (8) (1.3-93.8) | 66 (8) (10-99) | 77.8 (6) (63.8-93.3) |
| Blutron Plus (IPU 250g + DFF 100g) | 0.75 | 55.3 (7) (32.5-87) | 62.9 (8) (2.5-94.8) | 72.5 (8) (1 5-99) | 8 5 (6) (72.5-96.8) |

Figure 3

| Trial ID | Weeds | Efficacy >85% (Y/N) | Efficacy of Blutron (IPU 250g + DFF 50g) vs Standards (Higher/Lower/Comparable/Similar) | | | | |
|---|---|---|---|---|---|---|---|
| | | | Efficacy vs Arelon (IPU 250g) | Efficacy vs TransCel (IPU 250g) | Efficacy vs DFF (50g) | Efficacy vs Pendimethalin | Efficacy vs Picona |
| Pre emergence | | | | | | | |
| S11-03313-04 | POAAN | Y | Higher* | Comparable | Comparable | Comparable | Comparable |
| | STEME (<2 %GC) | Y | Higher* | Higher* | Comparable | Higher* | Comparable |
| | VERPE | Y | Higher* | Comparable | Comparable | Comparable | Comparable |
| | SENVU | Y | Higher* | Similar | Comparable | Higher | Comparable |
| | POAAN | Y | Higher* | Higher* | Comparable | Comparable | Similar |
| S11-03313-05 | SINAR | Y | Higher | Higher | Comparable | Higher | Similar |
| | VERHE | Y | Higher* | Higher | Comparable | Comparable | Comparable |
| | POAAN | Y | Higher* | Similar | Higher* | Higher | Similar |
| S11-03313-06 | SENVU | Y | Higher* | Higher* | Similar | Higher* | Similar |
| | STEME (<5 plts/m²) | Y | Higher* | Similar | Similar | Similar | Similar |
| | POAAN | Y | Higher* | Higher* | Comparable | Comparable | Comparable |
| S11-03313-01 | FUMOF | N | | | | Lower * | Lower * |
| | GALAP | N | | | | Comparable | Lower * |
| | POAAN | Y | Higher | | Similar | Comparable | - |
| | MATSS | Y | Higher* | | Similar | Comparable | - |
| S11-03314-02 | URTUR | Y | Higher* | | Similar | Comparable | - |
| | SENVU | Y | Higher* | | Similar | Comparable | - |
| | CAPBP | Y | Higher* | | Similar | Comparable | - |
| | POAAN | Y | Higher* | | Higher*(1st ass.timing) | Similar | - |
| S11-03314-06 | STEME | Y | Higher* | | Similar | Comparable | - |
| | MATCH | Y | Higher* | | Similar | Comparable | - |
| | POAAN | N | Higher* | | inconsistent | Lower* | - |
| | STEME | Y | Higher* | | Higher* | Similar | - |
| S11-03314-08 | CIRAR | Y | Higher* | | Higher* | Similar | - |
| | CHEAL | Y | Higher* | | Higher* | Similar | - |
| | RUMOB | Y | Higher* | | Higher* | Similar | - |
| | GALAP | Y | Higher* | | Higher* | Similar | - |

Figure 4

| Trial ID | Weeds | Efficacy >85% (Y/N) | Efficacy of Blutron (IPU 250g + DFF 50g) vs Standards (Higher/Lower/Comparable/Similar) | | | | |
|---|---|---|---|---|---|---|---|
| | | | Efficacy vs Arelon (IPU 250g) | Efficacy vs IPU TransCel (IPU 250g) | Efficacy vs DFF (50g) | Efficacy vs Pendimethalin | Efficacy vs Picona |
| S11-03314-10 | POAAN | Y | Higher* | | Higher | Comparable | - |
| | VEROF | Y | Higher* | | Higher* | Comparable | - |
| | VIOAR | Y | Higher* | - | Comparable | Comparable | - |
| S11-03314-12 | POAAN | Y | Similar | - | Comparable | Comparable | - |
| | MATIN | Y | Higher* | - | Higher* | Comparable | - |
| | POAAN | Y | Higher* (2nd ass.t) | - | Higher* (2nd ass.t) | Comparable | - |
| S11-03314-14 | STEME | Y | Higher* | - | Higher* | Comparable | - |
| | GERDI (<5 pl/m²) | Y | Higher* | - | Higher | Comparable | - |
| | VERPE | Y | Higher* | - | Similar | Comparable | - |
| Post emergence | | | | | | | |
| S11-033315-01 | POAAN | Y | Comparable | Higher | Higher* | Comparable | Comparable |
| | GALAP | N | Higher* | Higher* | Higher (last asse.t) | Comparable | Comparable |
| | FUMOF | N | Higher* | Similar | Higher* (last asse.t) | Lower | Lower |
| S11-033315-03 | POAAN | Y | Higher* | Lower* | Higher* | Comparable | Comparable |
| | MATCH | Y | Higher* | Higher | Similar | Similar | Comparable |
| | GALAP | Y | Higher | Higher* | Similar | Comparable | Higher* |
| S11-033315-02 | POAAN (high population) | N | Similar | Similar | Higher* (last asse.t) | Lower* (last asse.t) | Lower* (last asse.t) |
| S11-03316-01 | POAAN | N | Similar | - | Higher* | - | - |
| | POAAN | N | Lower* | - | Higher* | Comparable | - |
| S11-03317-02 | STEME | N | Similar | - | Similar | Comparable | - |
| | URTUR | N | Similar | - | Higher* | Higher* | - |
| S11-03317-03 | POAAN | Y | Comparable | - | Higher* | Comparable | - |
| S11-03317-04 | POAAN | Y | Comparable | - | Higher* | Comparable | - |
| | PAPRH | Y | Higher* | - | Higher* | Similar | - |
| | POAAN | N | Lower* | - | Comparable | Lower* | - |
| S11-03317-01 | GALAP | Y | Higher* (last ass.t) | - | Comparable | Similar | - |
| | VERPE | Y | Comparable | - | Comparable | Comparable | - |

Figure 4 - Continued

| Trial ID | Weeds | Efficacy >85% (Y/N) | Efficacy of Blutron (IPU 250g + DFF 50g) vs Standards (Higher/Lower/Comparable/Similar) | | | | |
|---|---|---|---|---|---|---|---|
| | | | Efficacy vs Arelon (IPU 250g) | Efficacy vs IPU TransCel (IPU 250g) | Efficacy vs DFF (50g) | Efficacy vs Pendimethalin | Efficacy vs Picona |
| S11-03317-05 | POAAN | N | Higher* | - | Comparable | Lower* | - |
| | PLASS | Y | Higher* | - | Similar | Comparable | - |
| | VEROF | Y | Higher* | - | Higher | Comparable | - |
| | URTDI | Y | Comparable | - | Higher* | Higher (last ass.t) | - |
| | BRSNN | Y | Higher | - | Higher | Comparable | - |
| | PAPSS | N | Similar | - | Similar | Lower | - |
| | CAPBP | Y | Higher* | - | Higher | Comparable | - |
| | VIOAR | Y | Higher* | - | Comparable | Comparable | - |

Figure 4 - Continued

| Trial ID | Weeds | Efficacy >85% (Y/N) | Efficacy of Blutron (IPU 250g + DFF 100g) vs Standards (Higher/Lower/Comparable/Similar) | | | | |
|---|---|---|---|---|---|---|---|
| | | | Efficacy vs Arelon (IPU 250g) | Efficacy vs IPU TransCel (IPU 250g) | Efficacy vs DFF (100g) | Efficacy vs Pendimethalin | Efficacy vs Picona |
| Pre emergence | | | | | | | |
| S11-03313-04 | POAAN | Y | Higher* | Comparable | Comparable | Comparable | Comparable |
| | STEME (<2 %GC) | Y | Higher* | Higher* | Comparable | Higher* | Comparable |
| | VERPE | Y | Higher* | Comparable | Comparable | Comparable | Comparable |
| | SENVU | Y | Higher* | Similar | Comparable | Higher | Comparable |
| | POAAN | Y | Higher* | Higher* | Higher | Similar | Comparable |
| S11-03313-05 | SINAR | Y | Higher | Higher | Comparable | Higher | Similar |
| | VERHE | Y | Higher* | Higher | Comparable | Comparable | Comparable |
| | POAAN | Y | Higher* | Similar | Higher* | Higher | Similar |
| S11-03313-06 | SENVU | Y | Higher* | Higher* | Similar | Higher* | Similar |
| | STEME (<5 plts/m²) | Y | Higher* | Similar | Similar | Similar | Similar |
| | POAAN | Y | Higher* | Higher* | Comparable | Comparable | Comparable |
| S11-03313-01 | FUMOF | N | | | | Lower* | Lower* |
| | GALAP | N | | | | Comparable | Lower* |
| | POAAN | Y | Higher | | Similar | Comparable | , |
| | MATSS | Y | Higher* | , | Similar | Comparable | , |
| S11-03314-02 | URTUR | Y | Higher* | , | Similar | Comparable | , |
| | SENVU | Y | Higher* | , | Similar | Comparable | , |
| | CAPBP | Y | Higher* | , | Similar | Comparable | , |
| | POAAN | Y | Higher* | , | Higher* | Similar | , |
| S11-03314-06 | STEME | Y | Higher* | , | Similar | Comparable | , |
| | MATCH | Y | Higher* | , | Similar | Comparable | , |
| | POAAN | Y | Higher* | , | Higher | Comparable | , |
| | STEME | Y | Higher* | , | Similar | Comparable | , |
| S11-03314-08 | CIRAR | Y | Higher* | , | Similar | Comparable | , |
| | CHEAL | Y | Higher* | , | Similar | Comparable | , |
| | RUMOB | Y | Higher* | , | Similar | Comparable | , |
| | GALAP | Y | Higher* | , | Similar | Comparable | , |

Figure 5

| Trial ID | Weeds | Efficacy >85% (Y/N) | Efficacy of Blutron (IPU 250g + DFF 100g) vs Standards (Higher/Lower/Comparable/Similar) | | | | |
|---|---|---|---|---|---|---|---|
| | | | Efficacy vs Arelon (IPU 250g) | Efficacy vs IPU TransCel (IPU 250g) | Efficacy vs DFF (100g) | Efficacy vs Pendimethalin | Efficacy vsPicona |
| S11-03314-10 | POAAN | Y | Higher* | - | Higher | Comparable | - |
| | VEROF | Y | Higher* | - | Comparable | Comparable | - |
| | VIOAR | Y | Higher* | - | Comparable | Comparable | - |
| S11-03314-12 | POAAN | Y | Higher* | - | Comparable | Comparable | - |
| | MATIN | Y | Higher* | - | Similar | Comparable | - |
| | POAAN | Y | Higher* | - | Higher* (2nd ass.t) | Comparable | - |
| | STEME | Y | Higher* | - | Higher* | Comparable | - |
| S11-03314-14 | GERDI (< 5 pl/m²) | Y | Higher* | - | Higher | Comparable | - |
| | VERPE | Y | Higher* | - | Similar | Comparable | - |
| Post emergence | | | | | | | |
| S11-03315-01 | POAAN | Y | Comparable | Higher | Higher* | Comparable | Comparable |
| | GALAP | N | Higher* | Similar | Similar | Lower | Lower |
| | FUMOF | N | Higher* | Similar | Comparable | Lower* | Lower |
| S11-03315-03 | POAAN | Y | Higher* | Higher* (last asse.t) | Comparable | Higher* (last asse.t) | Higher* (last asse.t) |
| | MATCH | Y | Higher* (last asse.t) | Similar | Lower* | Similar | Similar |
| | GALAP | Y | Higher* (last asse.t) | Higher* (last asse.t) | Lower* | Higher* (last asse.t) | Higher* (last asse.t) |
| S11-03315-02 | POAAN (high population) | N | Similar | Similar | Similar | Lower* (last asse.t) | Lower* (last asse.t) |
| S11-03316-01 | POAAN | N | Higher | - | Higher* | - | - |
| | POAAN | N | Similar | - | Higher* | Higher* | - |
| S11-03317-02 | STEME | N | Similar | - | Comparable | Comparable | - |
| | URTUR | Y | Comparable | - | Higher* | Higher* | - |
| S11-03317-03 | POAAN | Y | Comparable | - | Higher* | Comparable | - |
| | POAAN | Y | Comparable | - | Higher* | Comparable | - |
| S11-03317-04 | PAPRH | Y | Higher* | - | Higher* | Similar | - |
| | POAAN | N | Comparable | - | Higher* | Similar | - |
| S11-03317-01 | GALAP | Y | Higher* (last ass.t) | - | Comparable | Similar | - |
| | VERPE | Y | Comparable | - | Comparable | Comparable | - |

Figure 5 - Continued

| Trial ID | Weeds | Efficacy >85% (Y/N) | Efficacy of Blutron (IPU 250g + DFF 100g) vs Standards (Higher/Lower/Comparable/Similar) | | | | |
|---|---|---|---|---|---|---|---|
| | | | Efficacy vs Arelon (IPU 250g) | Efficacy vs IPU TransCel (IPU 250g) | Efficacy vs DFF (100g) | Efficacy vs Pendimethalin | Efficacy vs Picona |
| S11-03317-05 | POAAN | N | Higher* | - | Higher* | Similar | - |
| | PLASS | Y | Higher* | | Higher | Higher | - |
| | VEROF | Y | Higher* | - | Higher | Similar | - |
| | URTDI | Y | Comparable | - | Higher* | Higher (last asse.t) | - |
| | BRSNN | Y | Higher | - | Higher | Comparable | - |
| | PAPSS | N | Similar | - | Higher* | Lower | - |
| | CAPBP | Y | Higher* | - | Similar | Comparable | - |
| | VIOAR | Y | Higher* | - | Similar | Comparable | - |

Figure 5 - Continued

| Days After Application | 10-20 DA-A | 21-50 DA-A | 51-80 DA-A | >81DA-A |
|---|---|---|---|---|
| | Efficacy as mean % control (number of trials assessed at this timing) (minimum-maximum% control range) | | | |
| POAAN-Pre emergence (Blutron) | | | | |
| Blutron (IPU 250g + DFF 50g) | 66.7 (3) (25-100) | 88 (9) (59.8-99.5) | 87 (3) (68.5-100) | 90.4 (10) (62.5-100) |
| Hurricane SC (DFF 50g) | 40.8 (3) (17.5-77.5) | 75.9 (9) (51.5-99) | 88.3 (3) (71.5-99.5) | 76.2 (10) (28.8-98.8) |
| POAAN-Post emergence (Blutron) | | | | |
| Blutron (IPU 250g + DFF 50g) | 51.3 (7) (32.5-85.5) | 62.1 (8) (8.3-98.5) | 70.8 (8) (11.3-96.8) | 75.1 (6) (40-99.3) |
| Hurricane SC (DFF 50g) | 27.9 (7) (1.3-72.5) | 27.8 (8) (0-85) | 35.5 (8) (2.5-86.5) | 45.4 (6) (0-73.8) |
| POAAN-Pre emergence (Blutron plus) | | | | |
| Blutron Plus (IPU 250g + DFF 100g) | 71.7 (3) (30-100) | 94 (9) (82.5-99.8) | 97.7 (3) (95.3-99.5) | 96.2 (10) (77.5-100) |
| Hurricane SC (DFF 100g) | 57.4 (3) (27.5-74.8) | 82.7 (9) (54.3-99) | 97.8 (3) (94.5-99.8) | 91 (10) (68.8-99) |
| POAAN-Post emergence (Blutron plus) | | | | |
| Blutron Plus (IPU 250g + DFF 100g) | 55.3 (7) (32.5-87) | 62.9 (8) (2.5-94.8) | 72.5 (8) (15-99) | 85 (6) (72.5-96.8) |
| Hurricane SC (DFF 100g) | 44.3 (7) (6.3-99) | 28.3 (8) (0-99) | 43.8 (8) (6.8-98.5) | 47.3 (6) (5-72.5) |

Figure 6

PESTICIDE NANO-SUSPENSION

RELATED APPLICATIONS

This application is a 35 U.S.C. § 371 filing of International Application No. PCT/GB2013/052497, filed Sep. 24, 2013, which claims priority to Great Britain Patent Application No. 1217441.3, filed Sep. 28, 2012, each of which is incorporated herein by reference in its entirety.

The present invention relates to aqueous dispersions of active agents such as insecticides, herbicides and fungicides. In particular the present invention relates to such dispersions in which the particles are of sub-micron diameter.

Many active agents, such as insecticides, herbicides and fungicides are relatively insoluble in aqueous media. In order to apply them efficiently to crops it is thus necessary to formulate them in a manner that facilitates their dilution in the water based spray media used in practice, by the farmer or contract spray operator. Active agents that are relatively insoluble in aqueous media can often be dissolved in organic solvents which are then emulsified, with the use of suitable surface active agents, in the aqueous spray media. This type of formulation is known as an emulsifiable concentrate (EC). This is undesirable for the purposes of applying these agents to crops because of the negative environmental impact and the health risks associated with exposure to many such organic solvents. Organic solvents also add unnecessary cost to the formulation.

Relatively insoluble active agents may be formulated in a manner, so as to enable the application of the agent to the crops, as a colloidal suspension in water. Such colloidal suspensions can be formed by the dilution of the formulation, (containing suitable surface active agents), in the form of a water dispersible powder (WP), a suspension concentrate (SC), or a water dispersible granule (WG). Alternatively, the active may be encapsulated in a polymer wall and such a capsule suspension (CS) diluted for use as a colloidal aqueous spray.

The mean particle diameter of suspensions diluted from WP, SC, WG and CS formulations of active agents, are in the micron range, with typical mean values of between 1-5 microns. This value provides the physical stability on dilution, with the use of suitable surface active agents, that is sufficient to ensure a maintenance of the concentration of the active agent, i.e. minimal settling, without blocking of the spray nozzles during the spray application of the active agent to the crop being treated.

It is well known that the rate of dissolution of an active agent is related to, amongst other properties, the particle size distribution of the active agent, with a smaller mean particle size distribution providing an increase in the rate of solubility.

It is also known that insoluble active agents with mean particle size distributions in the nano-sized range, might provide superior properties, with regard to the mobility of such active agents across cell walls, so that the active agent may better penetrate the pests, against which these agents are active. It may therefore be advantageous to provide a composition comprising active agents, such as insecticides, herbicides and fungicides, that provide a stable aqueous dispersion of such active agents on dilution, with a small mean particle size.

Accordingly the present invention provides a composition, comprising an aqueous dispersion of particles, wherein the composition additionally comprises one or more active agents selected from: insecticides, herbicides and fungicides, together with a suitable surface active agent, and a process for producing such a composition.

The mean particle diameter of particles in the composition may be less than 500 nm, or more preferably less than 300 nm. The particles in the composition will also preferably have a narrow distribution of particles diameters, so that none are in the micron range. The particle size distribution of the composition described in this specification is typically measured by Dynamic Light Scattering (DLS), sometimes called Photon Correlation Spectroscopy (PCS) or Quasi-Elastic Light Scattering (QELS) and is the only technique able to measure particles in dispersion in a fast, routine manner with little or no sample preparation. The preparation required for other techniques can change the properties of the particles, for example aggregates can be created or destroyed.

The advantage of having small particles, for example particles of diameter less than 500 nm or preferably less than 300 nm, is that they are more easily able to penetrate cell walls and also have a more rapid rate of dissolution in water. They therefore demonstrate the required biological effect against the pest, with a smaller dose of the active agent. This means that less of the active agent needs to be applied, which is advantageous in terms of cost and in terms of reducing the effect of active agents on non-target organisms.

A major problem with producing a composition of an active agent with such a small particle size distribution, is that as the particle size is reduced, the charge density on the surface of the particle increases, such that the short range attractive forces thus produced, lead to the irreversible agglomeration of the particles, both during the particle size reduction process and on storage shortly after.

It is known that, for conventional dispersions in the micron range of particle size, there are two means of stabilising particles, namely by charge and steric stabilisation, using dispersants. These types of surfactant modify the surface charge of the particle, the zeta potential, so that a repulsive force thus produced, prevents the agglomeration that leads to the increase in mean particle size and thus settling of the active agent on storage. The degree and type of charge desired (more than +30 mV, or less than −30 mV for charge stabilisation and zero for steric stabilisation), can be measured using standard techniques, for example using a Malvern Zetasizer Nano-ZS machine.

It was found that, in the case of dispersions in the sub-micron range, surfactants known to those skilled in the art, although producing the required zeta potential values (more than +30 mV, or less than −30 mV) for the particles in the micron sized range, were not suitable for use, to allow the production of the sub-micron particles desired. The use of charge stabilisation led to a high degree of flocculation and the addition of further dispersant to replace the depleted amount as the particle size reduced and thus surface area increased, did not prevent irreversible agglomeration of the particles formed on milling. Similarly, when steric stabilisation techniques were applied, the polymeric dispersants employed by those skilled in the art, were not effective, even though they produced the neutral charge for particles in the micron sized range. The addition of additional polymeric dispersant to replace the depleted amount as the particle size reduced and thus surface area increased, simply led to an increase in viscosity and thus made the reduction in particle size impossible.

Surprisingly, it was discovered that when a composition comprising a dispersion of an active agent, isoproturon, in a solution of a polyetheralkanolamine comb polymer (Jeffsperse X3204) was milled, using a suitable micro-media mill containing suitable grinding media, a mean particle size of less than 300 nm was obtained. More surprisingly, the suspension thus obtained was stable for an extended period of time with no irreversible agglomeration or crystal growth and with no change in the mean particle size. Even more surprisingly, when this composition was diluted and applied to a crop, the rate of use of the active could be significantly reduced, maintaining an excellent degree of control of the pest against which isoproturon is active, with a reduced effect on non-target organisms.

It will be apparent to those skilled in the art, by the examples contained herein, the advantages of the invention described in this specification, together with the scope of the said invention.

The composition may comprise one or more herbicides which may be any herbicide having a solubility in water of less than 100 ppm. The herbicide may have a crystalline phase and a melting point sufficiently high that it does not melt during mechanical milling, for example with glass beads, to reduce the size of the particles.

The one or more herbicides may be selected from:

Atrazine, bromoxynil, butafenacil, buturon, cafenstrole, chlomethoxyfen, chlorflurenol-methyl, chlornitrofen, chlorotoluron, chloroxuron, chlorphthalim, chlorthal-dimethyl, cinidon-ethyl, clomeprop, daimuron, desmedipham, dichlobenil, diclosulam, difenoxuron, diflufenican, diflufenzopyr, dimefuron, dinoterb, dipropetryn, diuron, flumetsulam, flumioxazin, flumipropyn, flupoxam, fluridone, flurtamone, fluthiacet-methyl, haloxyfop, ioxynil, isomethiozin, isoproturon, isoxaben, isoxaflutole, isoxapyrifop, karbutilate, lenacil, mefenacet, methabenzthiazuron, methazole, metosulam, naproanilide, neburon, nitralin, norflurazon, oryzalin, oxadiargyl, oxaziclomefone, penoxsulam, pentoxazone, perfluidone, phenisopam, phenmedipham, picolinafen, prodiamine, prometryn, propazine, propyzamide, pyraflufen-ethyl, pyrazolynate, pyrazoxyfen, pyribenzoxim, pyroxsulam, quinclorac, quinoclamine, saflufenacil, siduron, simazine, terbuthylazine, terbutryn, thidiazimin, thiencarbazone-methyl, tralkoxydim and trietazine, The composition may comprise one or more insecticides which may be any insecticide having a solubility in water of less than 100 ppm. The insecticide may have a crystalline phase and a melting point sufficiently high that it does not melt during mechanical milling, for example with glass beads, to reduce the size of the particles. The one or more insecticides may be selected from:

abamectin, beta-cyfluthrin, bistrifluron, buprofezin, chlorantraniliprole, chlorfenapyr, chlorfluazuron, chromafenozide, cyfluthrin, deltamethrin, diafenthiuron, diflubenzuron, fipronil, flubendiamide, flucycloxuron, flufenoxuron, halofenozide, hexaflumuron, hydramethylnon, lufenuron, metaflumizone, methiocarb, methoxyfenozide, novaluron, noviflumuron, pyridaben, spinetoram, spinosad, spirotetramat, tebufenozide, teflubenzuron, thiodicarb, tralomethrin and triflumuron.

The composition may comprise one or more fungicides which may be any fungicide having a solubility in water of less than 100 ppm The fungicide may have a crystalline phase and a melting point sufficiently high that it does not melt during mechanical milling, for example with glass beads, to reduce the size of the particles.

The one or more fungicides may be selected from:

ametoctradin, amisulbrom, anilazine, azoxystrobin, benodanil, benomyl, benquinox, bitertanol, boscalide, captafol, captan, carbendazim, carpropamide, chinomethionat, chlobenthiazone, chloroneb, chlorothalonil, chlozolinate, copper hydroxide sulfate, cyazofamide, cyproconazole, dichlorfluanid, dichlone, dichlorophen, diclobutrazol, diclocymet, diclomezine, dicloran, diethofencarb, dimethomorph, dimoxystrobin, diniconazole, dithianon, epoxiconazole, famoxadone, fenamidone, fenarimol, fenbuconazole, fenfuram, fenhexamide, fenpiclonil, fludioxonil, fluopicolide, fluoroimide, fluotrimazole, fluoxastrobine, fluquinconazole, flusulfamide, flutianil, flutolanil, folpet, fuberidazole, halacrinate, hexaconazole, iprodione, iprovalicarb, kresoxim-methyl, mepanipyrim, metconazole, methfuroxam, myclozolin, nuarimol, oxpoconazole, pencycuron, procymidone, prothioconazole, quinoxyfen, quintozene, simeconazole, tebuconazole, thiabendazole, thifluzamide, thiophanate-methyl, thiram, triadimenol, triticonazole, valifenalate The composition may comprise two or more herbicides. The composition may comprise two or more insecticides. The composition may comprise two or more fungicides. The composition may comprise a mixture of active agents comprising one or more herbicides and/or with one or more insecticides and/or one or more fungicides. The composition may comprise two or more, three or more, four or more, five or more active agents selected from herbicides, insecticides and fungicides.

The composition may comprise a mixture of isoproturon (3-(4-isopropylphenyl)-1,1-dimethylurea and diflufenican (N-(2,4-difluorophynyl)-2-[3-(trifluoromethyl)phenoxy]-3-pyridinecarboxamine.

The composition may further comprise an antifoam agent.

The composition may comprise at least 25% by weight of an active agent selected from the lists of herbicides, insecticides and fungicides and combinations of such listed herein. The surface active agent may be selected to provide particles with zero charge. The surface active agent may be a comb polymer. The surface active agent may be Jeffsperse X3204

The composition may comprise at least 25% by weight of one or more active ingredients, 30% by weight of one or more active ingredients, 40% by weight of one or more active ingredients, 50% by weight of one or more active ingredients. The surface active agent may be a comb polymer. The surface active agent may be a polyetheralkanolamine comb polymer.

The surface active agent may be any surface active agent that, combined with the active ingredients allows particles of a suitable size having a near zero surface charge to be produced. The suitable size may be less than 500 nm, preferably less than 300 nm. The particles may have a mean zero charge and a narrow charge distribution.

The composition may comprise 0.5-50% of each ingredient.

The viscosity of the composition may be less than 1000 cps, may be less than 800 cps, may be less than 500 cps or may be less than 200 cps.

The composition may comprise 23.0% 3-(4-isopropylphenyl)-1,1-dimethylurea, 9.2% N-(2,4-difluorophenyl)-2-[3-(trifluromethyl)phenoxy]-3-pyridinecarboxyamide, 18.1% Polyetheralkanolamine comb polymer (Jeffsperse X3204) and 0.9% Dimethylpolysiloxane fluid emulsion.

The composition may comprise no organic solvent.

A method of providing an aqueous dispersion of particles comprising one or more active agents and a surface active agent comprising the steps of:

a mixing one or more active agents having a solubility of less than 100 ppm with a surface active agent and a sufficient amount of water to give an aqueous dispersion comprising at least 25 wt percent active agent;

b reducing the mean diameter of particles in the aqueous dispersion to less than 300 nm by mechanical means, wherein the surface active agent is selected to provide particles with a mean zero charge.

The particles may have a mean zero charge and a narrow charge distribution, for example the charge distribution may be less than 10 mV, less than 5 mV or less than 3 mV.

A method of controlling pests or weeds comprising the step of diluting the composition provided herein with water and applying to a site an effective amount of the diluted composition.

A method of selecting a surface active agent for a composition provided herein comprising the step of:
i) selecting one or more active agents having an aqueous solubility of less than 100 ppm;
ii) selecting a surface active agent that provides the particles with a mean zero charge when the mean diameter of the particles in an aqueous dispersion is less than 300 nm.

Any combination of active agents and surface active agent may be tested to see if it provides particles of a suitable size with a mean zero charge or a near zero charge using methods known in the art. For example using the Malvern Zetasizer Nano-ZS machine as described herein. Particles suitable for use in the present invention have a solubility of less than 100 ppm in water.

Use of a comb polymer as a surface active agent in a composition comprising an aqueous dispersion of particles, wherein the particles comprise a surface active agent and one or more active agents selected from: herbicides, insecticides or fungicides.

The skilled man will appreciate that preferred features of any one embodiment and/or aspect of the invention may be applied to all other embodiments and/or aspects of the invention.

The present invention will be further described in more detail, by way of example only, with reference to the following figures in which:

FIG. 1—illustrates Zeta Potential Distribution for Jeffsperse X3204

FIG. 2—Efficacy data has been generated for the weed species in FIG. 2,

FIG. 3—shows minimum effective dose efficacy of Blutron and Blutron plus against Annual meadow grass (POAAN) weeds, FIG. 4—shows a summary of the efficacy of Blutron applied pre and post emergence against various annual grass and broad leaved weed species, FIG. 5—shows a summary of the efficacy of Blutron plus applied pre and post emergence against various annual grass and broad leaved weed species, FIG. 6—shows a Summary of the efficacy of Blutron and Blutron plus against Annual meadow grass (POAAN).

DEVELOPMENT AND MANUFACTURE OF ISOPROTURON 250 G/L AND DIFLUFENICAN 100 G/L NANO-SUSPENSION FORMULATION

A nano-suspension formulation containing 250 grams per liter of Isoproturon and 100 grams per liter of Diflufenican was made.

Introduction

The aim of this project was to develop a stable nano-suspension formulation which contained 250 grams per liter of Isoproturon and 100 grams per liter of Diflufenican which had an average particle size of 200 nm, in order to provide a formulation with improved properties on dilution and subsequent use.

A 2 step process was required to produce a nano-suspension formulation, i.e.

Step 1—High shear mixing

Step 2—Grinding

The initial step required the mixing of slurry of Isoproturon and Diflufenican formulation on the Silverson high shear mixer.

Secondly, the slurry was passed through the Dynomill using 300 to 400 μm diameter glass beads until the correct average particle size had been reached.

Nano-Suspension Preparation

Formulation

| Component | % w/w |
|---|---|
| 3-(4-isopropylphenyl)-1,1-dimethylurea (Isoproturon Technical - 98.5%) | 23.0 |
| N-(2,4-difluorophenyl)-2-[3-(trifluoromethyl)phenoxy]-3-pyridinecarboxamide (Diflufenican Technical - 99.0%) | 9.2 |
| Polyetheralkanolamine comb polymer (Jeffsperse X3204) | 18.1 |
| Dimethylpolysiloxane fluid emulsion (Rhodorsil 426R) | 0.9 |
| Water | 48.8 |
| | 100.0% |

The specific gravity for the above formulation is 1.102

Step 1—High Shear Mixing

The Isoproturon and Diflufenican slurry was formed by initially mixing the surfactants, anti-foam and tap water into a solution. Into this solution, unmilled Isoproturon and Diflufenican technical was added under stirring. The slurry was then formed by using a Silverson mixer, at maximum speed, for thirty minutes.

Step 2—Grinding

The prepared slurry was milled in the Dynomill filled to 85% capacity with 300-400 μm glass beads. The slurry was pumped through and recycled using the Autoclude Peristaltic Pump on setting 1. The grinding chamber was cooled with tap water. The grinding of the slurry typically took 3 hours.

Physical Chemical Properties

Test formulation 175-061, batch size 1000 g was prepared and tested

Appearance

| Sample | Appearance |
|---|---|
| 175-061 | White, mild odour, slightly viscous liquid |

Dispersibility

| Sample | No. of Inversions |
|---|---|
| 175-061 | 5 |

Suspensibility

| Sample | Suspensibilty |
|---|---|
| 175-061 | 100% |

Wet Sieve

| Sample | WS150 μm | WS75 μm |
|---|---|---|
| 175-061 | 0.01% | 0.03% |

Persistent Foam

| Sample | 10 seconds | 1 minute | 3 minutes | 12 minutes |
|---|---|---|---|---|
| 175-061 | 33 ml | 28 ml | 24 ml | 19 ml |

Particle Size

| Sample | D50 |
|---|---|
| 175-061 | 252 nm |

Operating Conditions for the Dyno-Mill KDL for the Manufacture of Isoproturon 250 g/L and Diflufenican 50 g/L (Blutron) Nano-Suspension Formulation.

Conditions used for milling the particles to the desired size.
Machine used: Dyno-Mill KDL
Chamber Volume: 600 ml
Bead Fill: 85%
Agitator Speed: 6000 rpm
Grinding Media: 300 μm-400 μm Diameter Glass Beads
Flow Rate: 2 liters per hour
Separating System: 100 μm Rotating Gap
Recycling: Yes (Continuous)
Batch Size: 1 liter
Making Zeta Potential Measurements Using the Malvern Zetasizer Nano-ZS Machine Measurement of zeta potentials in an aqueous medium.
Sample Preparation
Stock Solution A stock solution is prepared by weighing the following components directly into a McCrone Micronising Mill polythene grinding jar filled with 48 sintered corundum grinding elements:

| Component | % w/w | Batch(g) |
|---|---|---|
| Technical | 5.0 | 1.0 |
| Agrilan F502 | 0.5 | 0.1 |
| Rhodorsil 426R | 0.5 | 0.1 |
| HPLC Grade Water | 94.0 | 18.8 |

Seal the jar and put in the McCrone Micronising Mill for 30 minutes.
Blank Solution Into a 100 ml beaker, pipette 2 drops of stock solution into 50 ml of HPLC grade water. Mix well.
Sample Solutions Into a 100 ml beaker, pipette 2 drops of stock solution and 3 drops of surfactants solution (10%), into 50 ml of HPLC grade water. Mix well.

The following surfactants should be considered, however this is not an exhaustive list,
Anionic surfactants such as
Borresperse 3A
Galoryl DT505
Lomar D
Morwet D425
Cationic surfactants such as
Aerosol C-61
Darvan 7
Geropon SC/213
Non-ionic surfactants such as
Airvol
Atlox 4913
Triton X-100
Procedure 1. Switch on the Zetasizer by pressing the button located on the back of the machine.
2. Initialize the software by clicking on the Zetasizer icon located on the connected computers desktop.
3. Open or create a measurement file,
File→Open→Measurement File.
4. Fill a clear disposable zeta cell with prepared sample solution and insert into Zetasizer.
5. Select measurement type,
Measure→Start SOP→Zeta→Method.
6. Enter the sample details and click Start.
7. Record the mean zeta potential (mV), Kcps, and the number and type of peaks.
8. Readings should be taken at RT, 37° C. and 54° C.

Blutron (IPU 250 g+DFF 50 g)

Blutron applied pre and post emergence at the rate of 1.01 product/ha generally achieved good levels of control (>85%) of various annual grass and broad leaved weed species.

Against various weed species, Blutron applied pre and post emergence at rate of 1.01 product/ha (IPU 250 g+DFF 50 g) achieved significantly higher control compared to that of standard IPU formulations applied at approved label rates (Arelon, IPU 250 g and IPU TransCel, IPU 250 g).

The overall efficacy of Blutron applied PRE emergence at rate of 1.01 product/ha (IPU 250 g+DFF 50 g) was generally comparable and occasionally higher compared to that of standard DFF formulation applied at approved label rates (Hurricane SC, DFF 50 g).

The overall efficacy of Blutron applied POST emergence at rate of 1.01 product/ha (IPU 250 g+DFF 50 g) was generally higher or occasionally similar compared to that of standard DFF formulation applied at approved label rates (Hurricane SC, DFF 50 g).

The overall efficacy of Blutron applied PRE and POST emergence at rate of 1.01 product/ha (IPU 250 g+DFF 50 g) was comparable to that of standard reference products applied at approved label rates.

Blutron Plus (IPU 250 g+DFF 100 g)

Blutron applied pre and post emergence at the rate of 1.01 product/ha generally achieved good levels of control (>85%) of various annual grass and broad leaved weed species.

Against various weed species, Blutron plus applied pre and post emergence at rate of 1.01 product/ha (IPU 250 g+DFF 100 g) achieved significantly higher control compared to that of standard IPU formulations applied at approved label rates (Arelon, IPU 250 g and IPU TransCel, IPU 250 g).

The overall efficacy of Blutron plus applied PRE emergence at rate of 1.01 product/ha (IPU 250 g+DFF 100 g) was generally comparable and occasionally higher compared to that of standard DFF formulation applied at approved label rates (Hurricane SC, DFF 100 g).

The overall efficacy of Blutron plus applied POST emergence at rate of 1.01 product/ha (IPU 250 g+DFF 100 g) was generally higher or occasionally similar compared to that of standard DFF formulation applied at approved label rates (Hurricane SC, DFF 100 g).

The overall efficacy of Blutron plus applied PRE and POST emergence at rate of 1.01 product/ha (IPU 250 g+DFF 100 g) was comparable to that of standard reference products applied at approved label rates.

Blutron—Efficacy Against Annual Meadow Grass (POAAN)

Across 14 of the trials reviewed, Blutron applied pre and post emergence at the rate of 1.01 product/ha achieved good levels of control (>85%) of Annual meadow grass.

Across 5 trials, Blutron applied pre and post emergence at rate of 1.01 product/ha (IPU 250 g+DFF 50 g) achieved significantly higher control compared to that of standard DFF formulation applied at approved label rates (Hurricane SC, DFF 50 g).

Blutron Plus—Efficacy Against Annual Meadow Grass (POAAN)

Across 14 of the trials reviewed, Blutron plus applied pre and post emergence at the rate of 1.01 product/ha achieved good levels of control (>85%) of Annual meadow grass.

Across 7 trials, Blutron plus applied pre and post emergence at rate of 1.01 product/ha (IPU 250 g+DFF 100 g) achieved significantly higher control compared to that of standard DFF formulation applied at approved label rates (Hurricane SC, DFF 100 g)

Overall Conclusions

Overall dose response was evident for major weeds (POAAN, CIRAR, FUMOF, GERDI, GALAP, MATCH, PAPRH, STEME, URTDI, URTUR) across 13 of the trials.

The efficacy of Blutron applied pre and post emergence at rate of 1.01 product/ha against all weeds or for certain weeds within 8 trials, reached below 85%.

The efficacy of Blutron plus applied pre and post emergence at rate of 1.01 product/ha against all weeds or for certain weeds within 7 trials, reached below 85%.

Across 11 trials, the efficacy of Blutron applied pre and post emergence at rate of 1.01 product/ha against all weeds or for certain weeds was significantly higher than that of DFF formulation applied at equivalent rate (50 g ai/ha).

Across 9 trials, the efficacy of Blutron plus applied pre and post emergence at rate of 1.01 product/ha against all weeds or for certain weeds was significantly higher than that of DFF formulation applied at equivalent rate (100 g ai/ha).

Generally across all the trials, the efficacy of Blutron and Blutron plus applied pre and post emergence at rate of 1.01 product/ha against all weeds or for certain weeds was significantly higher than that of IPU formulations applied at equivalent rates (250 g ai/ha).

The efficacy of Blutron and Blutron plus applied pre and post emergence at rate of 1.01 product/ha against all weeds or for certain weeds was generally comparable to that of standard reference product applied at approved label rates.

Across four trials, Blutron and Blutron plus applied pre and post emergence at 1.01 product/ha and at twice these rates to simulate sprayer overlap, caused no significant persistent phytotoxic damage or effects on crop yield.

The invention claimed is:

1. A composition comprising an aqueous dispersion of particles, wherein the particles comprise a surface active agent and one or more active agents selected from herbicides, insecticides or fungicides, the mean particle diameter is 500 nanometers or less, the surface active agent is a polyetheralkanolamine comb polymer, and wherein the composition comprises at least 25% by weight of active agent.

2. The composition according to claim 1 wherein the mean particle diameter is 300 nanometers or less.

3. The composition according to claim 1 wherein the particles have a mean zero charge.

4. The composition according to claim 1 wherein the particles have a narrow charge distribution, wherein the charge distribution is less than 10 mV.

5. The composition according to claim 1 wherein each of the active agents has an aqueous solubility of less than 100 ppm.

6. The composition according to claim 1 wherein the one or more herbicides are selected from: atrazine, bromoxynil, butafenacil, buturon, cafenstrole, chlomethoxyfen, chlorflurenolmethyl, chlornitrofen, chlorotoluron, chloroxuron, chlorphthalim, chlorthaldimethyl, cinidon-ethyl, clomeprop, daimuron, desmedipham, dichlobenil, diclosulam, difenoxuron, diflufenican, diflufenzopyr, dimefuron, dinoterb, dipropetryn, diuron, flumetsulam, flumioxazin, flumipropyn, flupoxam, fluridone, flurtamone, fluthiacet-methyl, haloxyfop, ioxynil, isomethiozin, isoproturon, isoxaben, isoxaflutole, isoxapyrifop, karbutilate, lenacil, mefenacet, methabenzthiazuron, methazole, metosulam, naproanilide, neburon, nitralin, norflurazon, oryzalin, oxadiargyl, oxaziclomefone, penoxsulam, pentoxazone, perfluidone, phenisopam, phenmedipham, picolinafen, prodiamine, prometryn, propazine, propyzamide, pyraflufen-ethyl, pyrazolynate, pyrazoxyfen, pyribenzoxim, pyroxsulam, quinclorac, quinoclamine, saflufenacil, siduron, simazine, terbuthylazine, terbutryn, thidiazimin, thiencarbazone-methyl, tralkoxydim and trietazine.

7. The composition according to claim 1 wherein the one or more insecticides are selected from: abamectin, beta-cyfluthrin, bistrifluron, buprofezin, chlorantraniliprole, chlorfenapyr, chlorfluazuron, chromafenozide, cyfluthrin, deltamethrin, diafenthiuron, diflubenzuron, fipronil, flubendiamide, flucycloxuron, flufenoxuron, halofenozide, hexaflumuron, hydramethylnon, lufenuron, metaflumizone, methiocarb, methoxyfenozide, novaluron, noviflumuron, pyridaben, spinetoram, spinosad, spirotetramat, tebufenozide, teflubenzuron, thiodicarb, tralomethrin and triflumuron.

8. The composition according to claim 1 wherein the one or more fungicides are selected from: ametoctradin, amisulbrom, anilazine, azoxystrobin, benodanil, benomyl, benquinox, bitertanol, boscalide, captafol, captan, carbendazim, carpropamide, chinomethionat, chlobenthiazone, chloroneb, chlorothalonil, chlozolinate, copper hydroxide sulfate, cyazofamide, cyproconazole, dichlorfluanid, dichlone, dichlorophen, diclobutrazol, diclocymet, diclomezine, dicloran, diethofencarb, dimethomorph, dimoxystrobin, diniconazole, dithianon, epoxiconazole, famoxadone, fenamidone, fenarimol, fenbuconazole, fenfuram, fenhexamide, fenpiclonil, fludioxonil, fluopicolide, fluoroimide, fluotrimazole, fluoxastrobine, fluquinconazole, flusulfamide, flutianil, flutolanil, folpet, fuberidazole, halacrinate, hexaconazole, iprodione, iprovalicarb, kresoxim-methyl, mepanipyrim, metconazole, methfuroxam, myclozolin, nuarimol, oxpoconazole, pencycuron, procymidone, prothioconazole, quinoxyfen, quintozene, simeconazole, tebuconazole, thiabendazole, thifluzamide, thiophanate-methyl, thiram, triadimenol, triticonazole, and valifenalate.

9. The composition according to claim 1 wherein the composition comprises two or more active agents.

10. The composition according to claim 1 wherein the composition further comprises an antifoam agent.

11. The composition according to claim 1 wherein the composition comprises 0.5 to 50% of each ingredient.

12. The composition according to claim 1 wherein the viscosity of the composition is less than 1000 cps.

13. The composition according to claim 1 comprising 23.0% 3-(4-isopropylphenyl)-1,1-dimethylurea, 9.2% N-(2, 4-difluorophenyl)-2-[3-(trifluromethyl)-phenoxy]-3-pyridinecarboxyamide, 18.1% polyetheralkanolamine comb polymer and further comprising 0.9% dimethylpolysiloxane fluid emulsion.

14. The composition according to claim 1 wherein the composition does not comprise an organic solvent.

15. The composition according to claim 1 wherein the composition comprises isoproturon and diflufenican.

16. The composition according to claim 1 comprising 3-(4-isopropylphenyl)-1,1-dimethylurea, N-(2,4-difluorophenyl)-2-[3-(trifluromethyl)-phenoxy]-3-pyridinecarboxyamide, polyetheralkanolamine comb polymer and further comprising dimethylpolysiloxane fluid emulsion.

* * * * *